United States Patent [19]

Isogai et al.

[11] 3,981,909

[45] Sept. 21, 1976

[54] PROCESS FOR PRODUCING PER-P-TOLUIC ACID AND UTILIZING THE SAME

[75] Inventors: Nobuo Isogai; Takashi Okawa; Takako Takeda, all of Niigata, Japan

[73] Assignee: Mitsubishi Gas Chemical Company, Inc., Tokyo, Japan

[22] Filed: Mar. 27, 1975

[21] Appl. No.: 562,805

[30] Foreign Application Priority Data

Apr. 8, 1974 Japan.............................. 49-40799
June 26, 1974 Japan.............................. 49-73119
June 26, 1974 Japan.............................. 49-73120

[52] U.S. Cl. .................... 260/502 A; 260/348.5 L; 260/523 R; 260/523 A; 260/476 R
[51] Int. Cl.$^2$....................................... C07C 179/10
[58] Field of Search............. 260/502, 502 R, 502 A

[56] References Cited
UNITED STATES PATENTS 3,832,392   8/1974   Imamura........................ 260/502 A Primary Examiner—James O. Thomas, Jr.
Assistant Examiner—W. B. Lone
Attorney, Agent, or Firm—Armstrong, Nikaido & Wegner

[57] ABSTRACT p-Tolualdehyde freed from reaction-inhibiting substances is autooxidized by a gas containing molecular oxygen in an aliphatic ketone or fatty acid ester solvent under pressure in the absence of catalyst to produce per-p-toluic acid. The resulting per-p-toluic acid is brought into contact with a lower olefin in the absence of catalyst to produce p-toluic acid and an alkylene oxide at the same time, or said per-p-toluic acid is reacted with allyl alcohol to produce glycidol and p-toluic acid at the same time, and further the resulting glycidol is hydrolyzed to produce glycerin, or said per-p-toluic acid is reacted with methanol in the presence of an esterification catalyst to produce hydrogen peroxide and methyl p-toluate at the same time. The foregoing reactions can be carried out easily and safely in simple processes in high yields.

3 Claims, No Drawings

PROCESS FOR PRODUCING PER-P-TOLUIC ACID AND UTILIZING THE SAME

This invention relates to a process for producing per-p-toluic acid, or p-toluic acid or its derivative together with an alkylene oxide, or glycidol or hydrogen peroxide at the same time, utilizing the resulting per-p-toluic acid.

More particularly, the present invention relates to a process for producing per-p-toluic acid by autooxidizing p-tolualdehyde freed from reaction-inhibiting substances in advance by a gas containing molecular oxygen in an aliphatic ketone or fatty acid ester under pressure in the absence of catalyst, and a process for producing p-toluic acid and an alkylene oxide at the same time by contacting the resulting per-p-toluic acid with a lower olefin in the absence of catalyst, thereby epoxidizing the olefin and converting per-p-toluic acid to p-toluic acid, or producing glycidol and p-toluic acid at the same time by reacting the resulting per-p-toluic acid with allyl alcohol, or producing hydrogen peroxide and methyl p-toluate by reacting the resulting per-p-toluic acid with methanol in the presence of an esterification catalyst.

Generally, p-tolualdehyde is synthesized from richly and cheaply available toluene and carbon monoxide by the so-called Gatterman-Koch reaction in the presence of a catalyst of $HF-BF_3$ or $HCl-AlCl_3$ or the like.

In the present invention, said p-tolualdehyde is converted to per-p-toluic acid, and a lower olefin, especially ethylene or propylene is epoxidized by the resulting per-p-toluic acid to produce an alkylene oxide, which serves as a raw material for producing polyesters or polyurethanes and p-toluic acid, which serves as a raw material for producing terephthalic acid or dimethyl terephthalate, at the same time, or allyl alcohol is epoxidized by the resulting per-p-toluic acid to produce glycidol, and further the resulting glycidol is hydrolyzed to produce glycerin and said p-toluic acid at the same time, or said per-p-toluic acid is reacted with methanol to produce hydrogen peroxide and methyl p-toluate, which also serves as a raw material for producing terephthalic acid or dimethyl terephthalate. Said p-toluic acid itself can be utilized as photo-sensitive pigment, fluorescent dye, rust-proof agent, farm chemical, pigments, etc. Thus, the present invention has an industrial great significance, and a distinguished value in the effective utilization of resources.

It is well known to oxidize aldehydes by air or oxygen under the atmospheric pressure in an appropriate solvent in the absence of catalyst. However, the process has a low reaction rate and low peracid yield, and thus is not practical. Usually, in that process, air or oxygen in a partially oxidized state or ultraviolet-irradiated state must be used. However, the sufficient reaction rate and peracid yield are hard to obtain even in that state, and further there is a substantial restriction to the apparatus to be utilized, as well as there are various risks in the process. Therefore, said prior art process is not satisfactory in the sence of industrial application.

On the other hand, it is well known to produce a peracid from aldehyde, utilizing a catalyst of iron, cobalt, nickel, copper, chromium and vanadium system (British patent specification No. 864,803) or a catalyst of groups IIb, III, and IV of the periodic table (Japanese Patent Publication No. 22,569/72). These processes based on the utilization of the catalysts have an industrially considerably important value in the production of a peracid from the ordinary aldehydes.

However, when the synthesis of per-p-toluic acid is carried out by applying said catalyst to the oxidation of p-tolualdehyde, said catalyst promotes the oxidation of p-tolualdehyde, but acts, at the same time, as a catalyst for decomposing per-p-toluic acid.

That is to say, in the process for epoxidizing olefins by per-p-toluic acid, the presence of the catalyst for synthesizing peracids promotes the decomposition reaction of per-p-toluic acid, and consequently a proportion of per-p-toluic acid not utilized in the epoxidation reaction of olefins is increased, and an alkylene oxide yield is greatly reduced thereby. To suppress the decomposition of the formed per-p-toluic acid and maintain a higher yield of per-p-toluic acid, it is, therefore, necessary to use a large amount of a solvent and oxidize p-tolualdehyde in a state of dilute solution. For example, when a cobalt salt is used as the catalyst, it is necessary to use such an amount of the solvent as to keep the concentration of reactant p-tolualdehyde below 10% by weight to attain the per-p-toluic acid yield of 70% or more, and keep the once formed per-p-toluic acid relatively stably. However, even the addition of the catalyst does not assure so much high reaction rate, and the use of a large amount of the solvent makes a space-time-yield of per-p-toluic acid smaller. Consequently, the necessary capacity of the apparatus will be larger, and ultimately a larger expense will be required for recovering the large amount of the solvent. Thus, the prior art process for producing per-p-toluic acid from p-tolualdehyde is not always satisfactory in the industrial scale operation.

Epoxidation of olefin by per-p-toluic acid has not been reported so far, but it is known to use a catalyst of molybdenum and tungsten system or inorganic acid system, which is quite different from said catalyst system used in the synthesis of peracid, in the similar epoxidation reaction by peracetic acid or perbenzoic acid, and the presence of the catalyst for synthesizing peracid is not preferable as shown later in Comparative Examples. Therefore, when the catalyst for synthesizing peracid is used, it is necessary before the epoxidation reaction either to separate and remove the catalyst components used from the per-p-toluic acid product solution or to separate and recover per-p-toluic acid therefrom. However, no process has been known yet for removing per-p-toluic acid from the per-p-toluic acid product solution through simple operations without decomposition, and it is also impossible to separate per-p-toluic acid by distillation. Only process for the separation is a crystallization process, but its operation as well as apparatus for the crystallization is not simple, and the decomposition of per-p-toluic acid is inevitable and renders the recovery yield very low. That is, it is industrially impossible to separate per-p-toluic acid and the catalyst for synthesizing peracid individually from the per-p-toluic acid product solution.

For the foregoing reasons, development of a process for producing per-p-toluic acid from p-tolualdehyde in the absence of catalyst in an industrial scale has been desired for a long time.

Furthermore, in the epoxidation by peracetic acid, etc. benzene, halogenated hydrocarbon or acetic acid is selected as a solvent, and ketones or esters to be used in the production of peracid is regarded as inappropriate according to such a prevailing knowledge that the ketones or esters as a solvent for the epoxidation reaction will make the reaction rate very low. Therefore, it is necessary before the epoxidation to separate and recover the solvent used in the synthesis of peracid and per-p-toluic acid individually from the per-p-toluic acid product solution, and the individual separation and recovery have difficulties similar to those encountered in the individual separation of per-p-toluic acid and the catalyst.

As a result of extensive studies to overcome these difficulties, the present inventors have found that per-p-toluic acid can be produced with a sufficiently high reaction rate in good yield at a high concentration in a stable state by a gas containing molecular oxygen under pressure in a solvent of aliphatic ketone or fatty acid ester in the absence of catalyst, when a very small amount of some kinds of impurities contained in the reactant p-tolualdhyde is removed to less than definite allowable limits. Furthermore, the present inventors have found that per-p-toluic acid has a higher oxidizing ability than other peracids, and thus can readily epoxidize olefins without any special arrangement for catalyst and solvent, and consequently the epoxidation of olefins even by the per-p-toluic acid product solution as such can be carried out with a sufficiently high reaction rate, and an alkylene oxide and p-toluic acid can be produced in high yield.

As a process for producing glycidol by reacting a peroxide with allyl alcohol or producing glycerin by further hydrolysis of the resulting glycidol, it is known to produce acetic acid and glycerin from peracetic acid and allyl alcohol. Peracetic acid is industrially obtained by oxidizing acetaldehyde in the presence of an organic solvent or oxidizing acetic acid with hydrogen peroxide, but peracetic acid is unstable and explosive. Thus, it is very difficult to concentrate the peracetic acid to obtain it at a high concentration. Usually, peracetic acid is obtained as an organic solvent solution having a peracetic acid concentration of 10 to 50%, and containing a small amount of acetic acid. However, when peracetic acid at such a low concentration is reacted with allyl alcohol, the reaction rate is low, and the resulting acetic acid reacts with glycidol or glycerin, thereby forming an ester. Furthermore, the organic solvent, unreacted methanol, glycerin, esters of glycerin and acetic acid, etc. show complicated distillation characteristics, and their separation is difficult to carry out. These are disadvantages encountered in the prior art.

It has been found in the present invention that these disadvantages can be overcome by reacting the per-p-toluic acid obtained in the manner as described above with allyl alcohol, thereby producing glycidol and p-toluic acid, separating p-toluic acid as crystals, then adding water to the resulting mother liquor, thereby converting glycidol to glycerin, and then distilling the mother liquor.

As a process for producing hydrogen peroxide by reacting a peroxide with methanol, it is known to produce methyl acetate and hydrogen peroxide from peracetic acid and methanol. However, peracetic acid is explosive, and it is difficult to obtain peracetic acid of high concentration, as described above. Thus, peracetic acid of low concentration must be used inevitably. However, the reaction of peracetic acid of low concentration with methanol proceeds at a low reaction rate, and the resulting methyl acetate has small uses. Furthermore, individual separation of methyl acetate, organic solvent, unreacted methanol, etc. is difficult to effect. Thus, the prior art has these disadvantages. It is found in the present invention that these disadvantages can be overcome by reacting the per-p-toluic acid obtained in the manner as described above with methanol in the presence of an esterification catalyst, thereby producing hydrogen peroxide and methyl p-toluate.

An object of the present invention is to provide a process for producing per-p-toluic acid, which comprises autooxidizing p-tolualdehyde freed from reaction-inhibiting substances with a gas containing molecular oxygen under pressure in an aliphatic ketone or fatty acid ester as a solvent in the absence of catalyst.

Another object of the present invention is to provide a process for simultaneously producing p-toluic acid and an alkylene oxide, which comprises autooxidizing p-tolualdehyde containing less than 300 ppm of aromatic hydrocarbons, less than 300 ppm of non-aromatic hydrocarbons, less than 300 ppm of high boiling point substances and less than 5 ppm of acidic substances in a form of solution having a concentration of 10 to 50% by weight in acetone or ethyl acetate as a solvent with a gas containing molecular oxygen under a pressure of 1 to 60 kg/cm$^2$ in the absence of catalyst, thereby producing per-p-toluic acid, and then contacting the resulting per-p-toluic acid with a lower olefin in the absence of catalyst.

Other object of the present invention is to provide a process for simultaneously producing p-toluic acid and glycidol, which comprises autooxidizing p-tolualdehyde containing less than 300 ppm of aromatic hydrocarbons, less than 300 ppm of non-aromatic hydrocarbons, less than 300 ppm of high boiling point substances and less than 5 ppm of acidic substances in a form of solution having a concentration of 10 to 50% by weight in acetone or ethyl acetate as a solvent with a gas containing molecular oxygen under a pressure of 1 to 60 kg/cm$^2$ in the absence of catalyst, thereby producing per-p-toluic acid, and then reacting the resulting per-p-toluic acid with allyl alcohol in the presence or absence of catalyst.

Further object of the present invention is to provide a process for simultaneously producing p-toluic acid and glycerin, which comprises autooxidizing p-tolualdehyde containing less than 300 ppm of aromatic hydrocarbons, less than 300 ppm of non-aromatic hydrocarbons, less than 300 ppm of high boiling point substances and less than 5 ppm of acidic substances in a form of solution having a concentration of 10 to 50% by weight in acetone or ethyl acetate as a solvent with a gas containing molecular oxygen under a pressure of 1 to 60 kg/cm$^2$ in the absence of catalyst, thereby producing per-p-toluic acid, then reacting the resulting per-p-toluic acid with allyl alcohol in the presence or absence of a catalytic amount of at least one compound of transition metal selected from Ti, V, Mo, W, Nb, Ta, Fe, Co, and Ni at a temperature of 30° to 100°C under the atmospheric pressure or under pressure, adding water directly to the resulting reaction product solution containing p-toluic acid and glycidol, or to a mother liquor after p-toluic acid is separated as crystals from the resulting reaction product solution, then distilling the mother liquor, thereby distilling off the solvent and unreacted allyl alcohol and hydrolyzing the glycidol to glycerin simultaneously, and separating deposited crytals of p-toluic acid from the mother liquor.

Still further object of the present invention is to provide a process for simultaneously producing methyl p-toluate and hydrogen peroxide, which comprises autooxidizing p-tolualdehyde containing less than 300 ppm of aromatic hydrocarbons, less than 300 ppm of non-aromatic hydrocarbons, less than 300 ppm of high boiling point substances and less than 5 ppm of acidic substances in a form of solution having a concentration of 10 to 50% by weight in acetone or ethyl acetate as a solvent with a gas containing molecular oxygen under a pressure of 1 to 60 kg/cm$^2$ in the absence of catalyst, thereby producing per-p-toluic acid, and reacting the resulting per-p-toluic acid with methanol in the presence of an esterification catalyst.

Now, the present invention will be described in detail below:

As described above, p-tolualdehyde, starting material of the present invention, is synthesized through reaction of toluene with carbon monoxide in the presence of a catalyst of HF—BF$_3$ or HCl—AlCl$_3$, and the resulting crude p-tolualdehyde is in a form of complex with the catalyst. After passage through the ordinary step of decomposing the complex, the crude p-tolualdehyde is purified to a purity of about 99% by distillation. The resulting p-tolualdehyde has a sufficient quality as an industrial raw material for the ordinary reaction processes other than the process of the present invention. That is, even if the resulting p-tolualdehyde as such is autooxidized with air under pressure in a solvent of acetone or ethyl acetate in the absence of catalyst, a long induction period is required for the start of reaction, and even if the reaction is started, a sufficient reaction rate cannot be obtained. Even with a sufficient time, the per-p-toluic acid yield is low, and thus the resulting p-tolualdehyde of purity of about 99% is not industrially preferable as the starting material for the present invention.

On the other hand, formation of peracids by autooxidation of aldehydes generally proceeds through radical chain reaction. In principle, radicals are generated only by air or heat, and thus it must be possible to produce peracids with a sufficient reaction rate especially without the presence of ozone or irradiation of ultraviolet rays, or without the presence of a catalyst.

The present inventors have made an extensive study on said grounds, taking into account a very small amount of impurities contained in said starting material p-tolualdehyde, and, as a result, the present inventors have confirmed that, among the impurities contained in p-tolualdehyde, a very small amount of aromatic hydrocarbons such as benzene, toluene, xylene, etc., non-aromatic hydrocarbons such as heptane, octane, etc. and high boiling point substances such as diphenylmethane, triallylmethane, etc. or further a very small amount of acidic substances such as HF, BF$_3$, etc. are substances causing the inhibition of autooxidation of p-tolualdehyde in the absence of catalyst.

In the autooxidation of p-tolualdehyde, the hydrocarbons existing as the impurities are converted to hydroperoxides by oxidation of said hydrocarbon itself by oxygen of by the per-p-toluic acid formed in a small amount, and the formed hydroperoxides are further decomposed to form phenolic compounds in the reaction system. On the other hand, the acidic substances contained in p-tolualdehyde decompose a portion of the formed per-p-toluic acid to form p-cresol, which promotes the decomposition of other hydroperoxides to the phenolic compounds. Even a very small amount of these phenols is formed to inhibit the progress of autooxidation reaction of p-tolualdehyde and lower the per-p-toluic acid yield.

As described above, p-tolualdehyde can be purified to a purity of about 99% by distillation, and the main impurity of the resulting p-tolualdehyde is o-tolualdehyde, which does not inhibit the practice of the present invention. The very small amount of impurities that inhibit the practice of the present invention are about 500 to about 1,000 ppm of aromatic hydrocarbons, about 200 to about 500 ppm of non-aromatic hydrocarbons, about 300 to about 1,500 ppm of high boiling point substances, and about 10 to about 20 ppm of acidic substances such as fluorine or chlorine compounds originated from the catalyst used in the synthesis of p-tolualdehyde.

To remove the very small amount of these reaction-inhibiting substances contained in the starting material p-tolualdehyde, it would be presumable to repeat precise distillation, but the precise distillation is not so effective, and industrially less efficient. As a result of various studies on the removal of the very small amount of these reaction-inhibiting substances, the present inventors have found that said reaction-inhibiting substances can be effectively removed by washing p-tolualdehyde with an aqueous solution of 5 to 10% by weight of sodium carbonate or potassium carbonate and then with water, separating an oil layer, and distilling the oil layer after dehydration, or adding about 0.5 part by weight of hexane to one part by weight of the oil layer to dissolve the oil layer into hexane after said alkali washing, water washing, oil layer separation and dehydration, and cooling the solution to a temperature below −10°C, thereby crystallizing out p-tolualdehyde.

Application of said purification procedure to the starting material p-tolualdehyde makes it readily possible to reduce or remove the reaction-inhibiting substances contained in the starting material p-tolualdehyde to the amounts ensuring the practice of the present invention without any trouble. The allowable amounts of the reaction-inhibiting substances in the starting material p-tolualdehyde for the practice of the present invention are less than 300 ppm, preferably less than 50 ppm for the aromatic hydrocarbons; less than 200 ppm, preferably less than 100 ppm for the non-aromatic hydrocarbons; less than 300 ppm, preferably less than 20 ppm for the high boiling point materials; and less than 5 ppm, preferably less than 1 ppm for the acidic substances.

So far as the p-tolualdehyde, which is purified by the ordinary from and further by the procedure as described above to reduce the amounts of the reaction-inhibiting substances to said allowable amounts, is used as the starting material for the present invention, a sufficiently satisfactory result can be obtained. to Synthesis of per-p-toluic acid by autooxidation reaction of p-tolualdehyde with a gas containing molecular oxygen under pressure in a solvent of aliphatic ketone or fatty acid ester in the absence of catalyst is carried out as follows:

The starting material p-tolualdehyde freed from the reaction-inhibiting substances by the purification treatment is prepared into a solution having a concentration of from 10 to 50%, preferably 10 to 40% by weight. In that case, acetone or ethyl acetate is usually selected as a solvent for the solution. Reaction proceeds even at a p-tolualdehyde concentration of less than 10% by weight, and a high per-p-toluic acid yield can be obtained, but the reaction rate is low, and a large amount of the solvent must be used. That is, the space-time yield of per-p-toluic acid is lowered, and thus the lower concentration than 10% by weight is not industrially preferable. On the other hand, the synthesis of per-p-toluic acid is sufficiently possible even at a p-tolualdehyde concentration of higher than 50% by weight, but the per-p-toluic acid yield is lowered to less than 70% by mole. This is because the amount of by-produced p-toluic acid is increased owing to the decomposition of the resulting per-p-toluic acid or the reaction of the resulting per-p-toluic acid with unreacted p-tolualdehyde promoted by the higher concentration of p-tolualdehyde. p-Toluic acid is deemed as a by-product in the production of per-p-toluic acid, but it is never a valueless compound, but has a sufficiently high industrial significance as a raw material for terephthalic acid. In fact, p-toluic acid is one of the ultimate products in the present invention, while other product is the alkylene oxide or glycidol. However, it is not preferable to convert p-tolualdehyde completely to p-toluic acid without effectively utilizing the oxidative ability of per-p-toluic acid, which is applicable to the epoxidazation of olefins or allyl alcohol. Therefore, in the practice of the present invention, it is preferable to make the starting material p-tolualdehyde concentration 50% by weight or less to obtain a high per-p-toluic acid yield. Furthermore, from the industrial point of view, it can be said that at the higher p-tolualdehyde concentration than 50% by weight a portion of the resulting per-p-toluic acid and a considerable portion of p-toluic acid are deposited as crystals, resulting in operational difficulty.

The autooxidation of p-tolualdehyde is carried out with a gas containing molecular oxygen, usually air under a pressure of 1 to 60 kg/cm² gage, preferably 20 to 40 kg/cm² gage, and a feed rate of the gas containing molecular oxygen depends upon the reaction conditions, but in any case a shortage of oxygen in the reaction system may not be a rate-controlling condition for the reaction. It is preferable to supply the gas containing molecular oxygen to the reaction system and purge a definite amount of the gas to the outside of the system without any interruption, thereby proceeding with the reaction under a constant pressure. Furthermore, it is necessary to sufficiently disperse the gas containing molecular oxygen to the reaction system so that the insufficient dispersion may not control the reaction rate. With the increasing pressure of the gas containing molecular oxygen, the reaction rate of p-tolualdehyde is increased, and the per-p-toluic acid yield is liable to be also increased. At the same time, eventual discharge of the solvent to the outside of the reaction system can be prevented thereby. Thus, it is appropriate for attaining the object of the present invention to carry out the autooxidation reaction under pressure. However, a pressure over 40 kg/cm² gage has no remarkable effect upon the increase in the reaction rate and per-p-toluic acid yield, and therefore it is desirable also from the standpoint of the industrial requirements for apparatus to carry out the autooxidation under a pressure of not more than 40 kg/cm² gage.

The autooxidation is carried out at a temperature of 10° to 50°C, preferably 20° to 40°C. At a lower temperature than 10°C, the reaction rate is low, whereas at a higher temperature than 50°C, formation of p-toluic acid by decomposition of the resulting per-p-toluic acid itself or by reaction of the resulting per-p-toluic acid with unreacted p-tolualdehyde is considerably increased, resulting in the decrease in per-p-toluic acid yield.

When p-tolualdehyde freed from the reaction-inhibiting substances is autooxidized in the absence of catalyst, while fulfilling said conditions of the present invention, the entire amount of p-tolualdehyde is completely reacted for a reaction time of 1 to 2 hours in per-p-toluic acid yield of 70 to 95% by mole. In that case, per-p-toluic acid can be obtained in a form of solution having a high concentration, for example, 10 to 40% by weight. The per-p-toluic acid thus obtained has a better stability than those obtained by other means. The by-products of the present autooxidation are substantially a small amount of p-toluic acid. Though p-toluic acid is a by-product in the production of per-p-toluic acid, it is one of the ultimate products in the present invention, and offers no problem at all.

Now, description will be made below of utilization of the per-p-toluic acid thus obtained.

First of all, description will be made below of a process for simultaneously producing an alkylene oxide and p-toluic acid by epoxidizing olefins with said per-p-toluic acid.

Olefin and the resulting per-p-toluic acid product solution containing 10 to 40% by weight of per-p-toluic acid and a small amount of p-toluic acid is fed into the reactor in the ratio of at least one mole of an olefin per mole of the per-p-toluic acid in the absence of catalyst, and the solution is sufficiently stirred in a tightly sealed system. Reaction is carried out at a temperature of 30° to 100°C, preferably 40° to 70°C. Even at a temperature below 30°C, the reaction can proceed, but the reaction rate is low. At a temperature above 100°C, decomposition of per-p-toluic acid readily takes place, and consequently the epoxidation ratio is unpreferably lowered.

Of course, the epoxidation proceeds when less than one mole of the olefin per mole of per-p-toluic acid is used, but ultimately some per-p-toluic acid remains as unreacted or decomposed while being not utilized in the epoxidation reaction. Therefore, the use of less than one mole of the olefin per mole of per-p-toluic acid is not preferable from the standpoint of effective utilization of per-p-toluic acid. That is, it is desirable to make at least one mole of the olefin per mole of per-p-toluic acid exist in the reaction system, but the use of more than 4 moles of the olefin is not particularly effective. Preferable examples of the olefin are ethylene and propylene.

When the olefin is epoxidized with the per-p-toluic acid, while fulfilling said conditions, the epoxidation is completed within one hour in alkylene oxide yield of 80% by mole or more and p-toluic acid yield of about 100% by mole, based on per-p-toluic acid. That is to say, the entire amount of per-p-toluic acid is consumed in the epoxidation reaction, and is converted to p-toluic acid, while 80% by mole or more of the per-p-toluic acid is effectively utilized in the epoxidization of the olefin in that process. In the present invention, the desired alkylene oxide and p-toluic acid can be readily obtained in high yield.

Furthermore, it is one of the distinguished features of the present invention that no other byproducts than the desired products are substantially formed. That is, no reaction takes place at all between the solvent of aliphatic ketone or fatty acid ester and the alkylene oxide, or between the solvent and p-toluic acid. p-Toluic acid has a high boiling point (275°C) and a high melting point (179.6°C), and is very difficult to purify or separate by distillation. However, according to the present invention, most of the resulting p-toluic acid can be readily separated as crystals, because p-toluic acid has a low solubility in the solvent, for example, its solubility in acetone at room temperature is about 12 g/100 g, and its solubility in ethyl acetate at room temperature is about 6 g/100 g. The resulting p-toluic acid is obtained in a solution state, depending upon the conditions, but even in that case p-toluic acid can be readily separated and recovered as crystals with a high purity through a recovery step by simple distillation of the solvent.

In addition to the foregoing fact, the concentration of p-toluic acid in solvent never exceeds its solubility, and is always kept low, and consequently, there is no substantial occurrence of esterification reaction of alkylene oxide, one of the desired products and p-toluic acid, another desired product. Furthermore, there is no catalyst, or no other acidic inorganic substance, or no acidic organic substance or no water in the reaction system, and consequently no ring-opening reaction of the alkylene oxide takes place, and formation of by-products can be prevented thereby.

Separation and recovery of the products resulting from the epoxidation reaction can be readily carried out. For example, when propylene is used as the olefin, separation and recovery of unreacted propylene can be carried out by distillation under pressure, separation and recovery of propylene oxide by distillation under the atmospheric pressure, and separation and reovery of the solvent used by simple distillation. Separation and recovery of p-toluic acid can be readily carried out, for example, by crystallization.

Now, description will be made below of a process for simultaneously producing glycidol and p-toluic acid by reaction of the resulting per-p-toluic acid with allyl alcohol, and producing gylcerin through hydrolyzation of the resulting glycidol.

Allyl alcohol to be used as the starting material for the present process can be synthesized according to various procedures, but it is most preferable to use the allyl alcohol prepared by epoxidizing propylene with per-p-toluic acid, thereby forming propylene oxide in the manner as described above, and isomerizing the resulting propylene oxide.

The per-p-toluic acid product solution containing 10 to 40% by weight of per-p-toluic acid and a small amount of p-toluic acid, obtained in the manner as described above, is used as such without distilling off the solvent, or, if necessary, in a form of crystals of per-p-toluic acid containing a small amount of p-toluic acid, which is obtained by distilling off the solvent. Per-p-toluic acid is more reactive than peracetic acid, and also stable and easy to handle.

In the present invention, allyl alcohol is added to the per-p-toluic acid product solution or crystals of per-p-toluic acid in the presence or absence of a catalyst, and the resulting mixture is thoroughly stirred in a tightly sealed system or a reactor provided with a reflux cooler. Reaction is carried out at a temperature of 30° to 100°C, preferably 40° to 70°C. The reaction can proceed even at a temperature below 30°C, but the reaction rate is low. At a temperature above 100°C, decomposition of per-p-toluic acid is liable to take place, and furthermore side reaction of the resulting glycidol is also liable to take place. Consequently, the epoxidation ratio is unpreferably lowered. The reaction can be carried out under the atmospheric pressure or under pressure. It is preferable to add at least one mole of allyl alcohol per one mole of per-p-toluic acid. The epoxidation can proceed even when less than one mole of allyl alcohol is added per one mole of per-p-toluic acid, but ultimately per-p-toluic acid remains as unreacted, or decomposed while being not utilized in the expoxidation reaction. Therefore, the addition of less than one mole of allyl alcohol is not appropriate from the standpoint of effective utilization of per-p-toluic acid. It is not especially necessary to set the upper limit amount to allyl alcohol to be added to per-p-toluic acid, but it is desirable in view of the recovery operation of unreacted allyl alcohol and space-time yield of epoxide to add not more than 4 moles of allyl alcohol per one mole of per-p-toluic acid.

It is preferable to use a solvent when the reaction is carried out. Any solvent can be used, so long as the solvent can dissolve per-p-toluic acid in a stable state and also can dissolve allyl alcohol. Especially preferable solvents are aliphatic ketones such as acetone and fatty acid esters such as ethyl acetate. Preferable concentration of per-p-toluic acid in the solvent is 10 to 40% by weight. Epoxidation reaction can proceed even at a per-p-toluic acid concentration below 10% by weight, and the epoxidation ratio is liable to be somewhat elevated, but the reaction rate is lowered and the space-time yield of epoxide is lowered. Thus, the use of the per-p-toluic acid concentration below 10% by weight is not preferable. At a per-p-toluic acid concentration above 40% by weight, the reaction rate is increased, but the decomposition ratio of per-p-toluic acid is liable to be increased, and the side reaction is very liable to take place. Furthermore, since per-p-toluic acid is ultimately converted to p-toluic acid in the present invention, and the resulting p-toluic acid is crystallized, and the concentration of the resulting slurry in the system is an important problem in the industrial operation, it is preferable to use the per-p-toluic acid concentration of not more than 40% by weight.

When the epoxidation reaction of allyl alcohol by per-p-toluic acid is carried out while fulfilling said conditions, the reaction is completed within two hours in glycidol of 80% or more and p-toluic acid yield of about 100%, based on per-p-toluic acid. It is not especially necessary to carry out the present reaction in the presence of a catalyst, but when a catalytic amount of at least one compound of transition metal selected from Ti, V, Mo, W, Nb, Ta, Fe, Co, Ni, etc. is added to the reaction system, some effect upon the reaction rate can be expected.

The respective components are separated and recovered from the reaction product solution of the present invention in the following manner.

p-Toluic acid has a low solubility in the solvent, as described above, and most of p-toluic acid can be readily separated as crystals. To one part by weight of mother liquor resulting from said separation, or said reaction product solution as such, if the formed p-toluic acid is still in a solution state, depending upon the epoxidation conditions, is added 0.5 to 1 part by weight of water. The resulting water-added solution is subjected to simple distillation under the atmospheric pressure to separate the solvent, unreacted allyl alcohol, and a portion of water, and then the resulting distillate is subjected to further rectification to separate and recover the solvent and the unreacted allyl alcohol individually. Through that operation, the glycidol contained in the epoxidation product solution is almost completely hydrolyzed to the desired product glycerin, which is completely extracted into a water layer of the bottoms. On the other hand, p-toluic acid dissolved in the solvent is almost completely deposited as crystals by the addition of such a large amount of water, because its solubility in water is nearly zero. Therefore, p-toluic acid can be separated and recovered in high yield by filtering the bottoms.

On the other hand, the resulting filtrate is an aqueous solution consisting substantially of glycerin, but there is a possibility to contain a very small amount of p-toluic acid or glycidol and a portion of esterified products therein, and therefore such a small amount of caustic soda (less than 0.5% by weight) as to make the solution weakly alkaline is added to the solution. Then, the solution is subjected to simple distillation to remove water, and after thorough dehydration undere a reduced pressure, the resulting residue is subjected to distillation under a reduced pressure, whereby glycerin of high quality can be recovered in high yiled.

Now, description will be made below of a process for simultaneously producing hydrogen peroxide and methyl p-toluate by reacting said per-p-toluic acid with methanol in the presence of an esterification catalyst.

To said reaction product solution of per-p-toluic acid obtained in the manner as described above, or crystals of per-p-toluic acid separated from the reaction product solution by distilling the solvent therefrom, is added methanol in the presence of an esterification catalyst, and the resulting mixture is thoroughly stirred in an autoclave of tightly sealed system or a atmospheric pressure reactor provided with a reflux cooler. Reaction is carried out at a temperature of 50° to 100°C, preferably 65° to 85°C. Even at a temperature below 50°C, the reaction can proceed, but its reaction rate is low. At a temperature above 100°C, decomposition of per-p-toluic acid is very liable to take place. Furthermore, decomposition of the resulting hydrogen peroxide is also very liable to take place, and the hydrogen peroxide yield is consequently lowered. Thus, it is not preferable to carry out the reaction at a temperature beyond said temperature range.

In the present reaction, as esterification catalyst is used. Examples of the esterification catalyst include sulfuric acid, hydrochloric acid, phosphoric acid, strongly acidic cation exchange resin, etc.

When sulfuric acid, hydrochloric acid or phosphoric acid is used as the catalyst, its amount is in a range of 0.1 to 10% by weight, preferably 0.5 to 5.0% by weight, based on the weight of reactants. When the strongly acidic cation exchange resin is used, it is preferable in view of reaction operation to carry out the reaction at a catalyst concentration of not more than 50% by weight, based on the weight of reactants. It is preferable to add at least 4 moles of methanol per one mole in total of per-p-toluic acid and p-toluic acid. The esterification reaction can proceed even if less than 4 moles of methanol is used, but a portion of unreacted p-toluic acid is crystallized in the reaction system in a state free from per-p-toluic acid after the completion of the reaction, and is formed into a slurry state. This is not preferable in the industrial operation.

When the per-p-toluic acid product solution is used, the reaction can be also carried out by continuously distilling off the solvent, for example, acetone at the same time when the reaction starts.

When the esterification reaction of methanol with per-p-toluic acid is carried out while fulfilling said conditions, the reaction is completed within three hours, and the entire amount of per-p-toluic acid is completely consumed. Hydrogen peroxide yield is 68% by mole or more, based on per-p-toluic acid, and methyl p-toluate yield is 80% by mole or more, based on the total amount of fed per-p-toluic acid and p-toluic acid contained in said per-p-toluic acid. On the other hand, p-toluic acid is obtained in yield of less than 20%, together with methyl p-toluate. p-Toluic acid is not harmful at all, even if it is retained in the product solution. However, p-toluic acid can be converted, if necessary, to methyl p-toluate by further esterification in the following manner, after hydrogen peroxide is separated from the product solution.

According to the present invention, methyl p-toluate, one of the desired products is very stable against hydrogen peroxide, and no by-products are substantially formed.

The respective components are separated and recovered from the esterification product solution in the following manner.

The reaction product solution obtained under said conditions is a homogeneous solution containing the desired products, hydrogen peroxide and methyl p-toluate, and unreacted methanol, p-toluic acid, catalyst and a small amount of water. The small amount of water contained therein is formed by the esterification of methanol with p-toluic acid. Therefore, hydrogen peroxide at a higher concentration, for example, 70% by weight or more, can be obtained, in principle, by distilling off methanol from the reaction product solution, but water is added thereto to prevent a risk of explosion. In the present invention hydrogen peroxide can be safely obtained at a concentration as high as about 50% by weight by adjusting the amount of water to be added in view of the explosion limit. That is to say, methanol can be readily recovered by distillation under the atmospheric pressure or a reduced pressure without any loss of hydrogen peroxide, and used again in the present reaction. The resulting residue solution is separated into two layers, that is, an organic layer of methyl p-toluate containing p-toluic acid and an aqueous layer of hydrogen peroxide, water and the catalyst. In the organic layer, several percents of hydrogen peroxide is distributed, but can be recovered by further addition of water to the organic layer after phase separation of the organic layer from the aqueous layer. On the other hand, in the aqueous layer, no methyl p-toluate or p-toluic acid is substantially contained, and thus hydrogen peroxide can be recovered by distilling the aqueous layer as such after said phase separation. If necessary, it is possible to concentrate hydrogen peroxide to a higher concentration according to the ordinary procedure.

When the strongly acidic cation exchange resin is used as the catalyst, it is desirable to carry out the separation and recovery of the respective components from the esterification product solution in the same manner as above, after the catalyst has been separated and recovered from the esterification product solution by filtration. When the per-p-toluic acid product solution is used, the separation and recovery of hydrogen peroxide and methyl p-toluate can be carried out in the same manner as above, after the solvent, for example, acetone, and methanol have been recovered individually by distillation.

According to the present invention, per-p-toluic acid having a good reactivity and stability is synthesized through p-tolualdehyde derived from toluene having a less industrial applicability, and the resulting per-p-toluic acid is reacted with a lower olefin to produce p-toluic acid and an alkylene oxide of a great industrial demand and high value, or reacted with allyl alcohol to produce p-toluic acid and glycidol or glycerin, or reacted with relatively cheap methanol to produce methyl p-toluate and hydrogen peroxide readily and safely in high yields through simple processes. Thus, the present invention has an industrially important significance.

Especially, when per-p-toluic acid is reacted with allyl alcohol, p-toluic acid has a low solubility in the solvent, and the p-toluic acid concentration can be kept always low in the solvent during the reaction. Consequently, no esterification reaction of p-toluic acid with glycidol substantially takes place. Furthermore, since there is no water in the reaction system, no ring-opening reaction of glycidol substantially takes place during the epoxidation reaction. For these reasons, by-products are hardly formed, and only p-toluic acid and glycerin of industrially great demand and high value can be obtained in high yields.

The present invention can be carried out not only batch-wise, but also continuously.

Now, the present invention will be explained in detail below, referring to examples and comparative examples.

EXAMPLE 1

One part by weight of p-tolualdehyde of high purity (99% or higher) obtained by synthesis and distillation according to the ordinary procedure is admixed with 0.5 parts by weight of an aqueous 10 wt. % sodium carbonate solution, and washed therewith stirring in a nitrogen atmosphere. Then, the resulting oil layer is separated, and washed twice with 0.5 parts by weight of pure water. Then, the oil layer is again separated, dehydrated with active alumina (Neobead, trademark of the product made by Mizusawa Kagaku K.K., Japan) and distilled to obtain p-tolualdehyde as a starting material for autooxidation. Then, 100 g (0.832 moles) of p-tolualdehyde resulting from said treatment is charged, together with 200 g of dehydrated acetone, into an autoclave having a capacity of 700 ml and a rotating stirrer made from stainless steel (SUS - 32), and a reflux cooler. Air is supplied to the autoclave under an air pressure of 30 kg/cm² gage in the absence of catalyst so that a purge gas rate may be 120 l/hr, and autooxidation is carried out at a reaction temperature of 28° to 30°C with a stirrer rotation speed of 700 rpm.

5 Minutes after the start of stirring, reaction is initiated, and the entire amount of charged p-tolualdehyde is oxidized for a reaction time of 2 hours. The resulting reaction product solution is slightly yellow and clear, and the total amount of the product solution is 323.9 g. Composition analysis of the product solution reveals that the solution contains 31.6% by weight of per-p-toluic acid and 6.61% by weight of p-toluic acid, and other by-products are hardly contained. Thus, 102.5 g (0.674 moles) per per-p-toluic acid is formed and corresponds to yield of 81.0% by mole, based on the charged p-tolualdehyde.

The product solution containing per-p-toluic acid undergoes no change, even if it is left standing at room temperature for 24 hours, and per-p-toluic acid can be kept stably for a long period of time.

EXAMPLE 2

0.5 Parts by weight of hexane is dissolved in one part by weight of p-tolualdehyde of high purity (99% or more) obtained according to the ordinary procedure, and then the resulting solution is admixed with 0.5 parts by weight of an aqueous 10 wt. % sodium carbonate solution, and washed therewith with stirring with a nitrogen atmosphere. An oil layer is separated from the resulting mixture and washed twice with 0.5 parts by weight of pure water. Then, the oil layer is again separated, and thoroughly dehydrated. Then, the oil layer is cooled to about −12°C to crystallize out p-tolualdehyde, and p-tolualdehyde is separated from hexane thereby. Then, the separated p-tolualdehyde is bubbled with a nitrogen gas at about 70°C to thoroughly remove light boiling components from p-tolualdehyde. The p-tolualdehyde thus obtained is used as a starting material for autooxidation.

Then, 100 g (0.832 moles) of p-tolualdehyde thus treated, and 200 g of dehydrated acetone are charged into an autoclave, and air if fed to the autoclave under an air pressure of 30 kg/cm² gage in the absence of catalyst at a purge gas rate of 120 l/hr. Autooxidation is carried out at a reaction temperature of 25° to 27°C at a stirrer speed of 700 rpm. Two minutes after the start of stirring, the reaction is initiated, and the entire amount of charged p-tolualdehyde is oxidized for a reaction time of 1.8 hours.

The resulting reaction product solution is slightly yellow and clear, and the total amount of the product solution is 324.5 g. The product solution contains 33.1% by weight of per-p-toluic acid and 5.24% by weight of p-toluic acid. Therefore, 107.4 g (0.706 moles) of per-p-toluic acid is formed, and corresponds to yield of 84.9% by mole, based on the charged p-tolualdehyde.

Even if the resulting product solution is left standing at room temperature for several days, decomposition of per-p-toluic acid is hardly observed.

EXAMPLE 3

50 g (0.416 moles) of p-tolualdehyde pretreated in the same manner as described in Example 2, and 200 g of dehydrated acetone are charged into an autoclave, and subjected to reaction in the absence of catalyst at a reaction temperature of 24° to 26°C with stirring at 700 rpm, while supplying air under air pressure of 48 kg/cm² gage at a purge gas rate of 60 l/hr.

5 Minutes after the start of stirring, the reaction is started, and the entire amount of charged p-tolualdehyde is completely oxidized for a reaction time of 2.5 hours.

The resulting reaction product solution is slightly yellow and clear, and the total amount of the product solution is 263.1 g. The product solution contains 23% by weight of per-p-toluic acid and 0.93% by weight of p-toluic acid. Therefore, 60.5 g (0.398 moles) of per-p-toluic acid is formed, and corresponds to yield of 95.7% by mole, based on the charged p-tolualdehyde.

The resulting reaction product solution is stable at room temperature for a prolonged period of time.

EXAMPLE 4

50 g (0.416 moles) of p-tolualdehyde pretreated in the same manner as in Example 2, and 200 g of dehydrated ethyl acetate are charged into an autoclave, and subjected to reaction in the absence of catalyst at a reaction temperature of 26° to 27°C with stirring at 700 rpm, while supplying air under air pressure of 30 kg/cm² gage at a purge gas rate of 60 l/hr.

8 Minutes after the start of stirring, the reaction is started, and the entire amount of charged p-tolualdehyde is oxidized for a reaction time of 3.2 hours.

The resulting reaction product solution is slightly yellow and clear, and the total amount of the product solution is 262.2 g. The product solution contains 19.9% by weight of per-p-toluic acid and 3.79% by weight of p-toluic acid. Therefore, 52.2 g (0.343 moles) pf per-p-toluic acid is formed, and corresponds to per-p-toluic acid yield of 82.5% by mole, based on the charged p-tolualdehyde.

The resulting product solution can be kept stably at room temperature.

EXAMPLE 5

Epoxidation of propylene is carried out with 250 g of the product solution containing 31.6% by weight of per-p-toluic acid obtained as such in Example 1. That is to say, the per-p-toluic acid product solution contains 79.0 g (0.519 moles) of per-p-toluic acid, 154.5 g of solvent acetone and 16.5 g (0.121 mole) of p-toluic acid. 87.5 g of propylene, which corresponds to 4 times the moles of per-p-toluic acid contained therein, is charged to an autoclave, and subjected to reaction for one hour in a tightly sealed system at a temperature of 50° to 52°C with stirring at 500 rpm. After the completion of reaction, the autoclave is cooled, and unreacted propylene is purged from the system, and recovered into a gas holder. After purging the autoclave with nitrogen, the contents of the autoclave is withdrawn. The entire amount of the content is 267.5 g. Then, the deposited crystals are filtered off, and dried, whereby 68.7 g of p-toluic acid is obtained. When the mother liquor is distilled, 25.7 g of propylene oxide is obtained, and 151 g of the solvent acetone is recovered. At the same time, 18.4 g of p-toluic acid is obtained as bottoms. Other by-products are hardly obtained.

Therefore, reaction selectivity to propylene oxide, based on the reacted per-p-toluic acid is 85.3% by mole. On the other hand, total 87.1 g of p-toluic acid is contained in the product. Upon deduction of the amount of p-toluic acid contained in advance in the fed product solution as the starting material, the amount of p-toluic acid newly formed by the epoxidation reaction is 70.6 g. Thus, the reacted per-p-toluic acid is converted to p-toluic acid with 100% selectivity.

EXAMPLE 6

Epoxidation of propylene is carried out with 200 g of the product solution containing 23% by weight of per-p-toluic acid obtained as such in Example 3. That is, the product solution contains 46 g (0.302 moles) of per-p-toluic acid, 152.2 g of solvent acetane, and 1.86 g (0.014 moles) of p-toluic acid. 50.7 g 1.20 mole) of propylene is fed to an autoclave containing said product solution, and subjected to reaction for 1 hour at a temperature of 68° to 70°C. Then, the autoclave is cooled, and unreacted propylene is recovered. After purging with nitrogen, the contents of the autoclave is withdrawn, and the total amount of the contents is 211.1 g.

When the entire amount of the contents is distilled, 15.9 g of propylene oxide is obtained. After the recovery of solvent acetone, 42.2 g of p-toluic acid is obtained as bottoms. Therefore, the selectivity to propylene oxide, based on the per-p-toluic acid, is 90.8% by mole, and the reacted per-p-toluic acid is almost all converted to p-toluic acid.

EXAMPLE 7

Epoxidation of propylene is carried out with 200 g of the product solution containing 19.9% by weight of per-p-toluic acid obtained as such in Example 4. That is, the product solution contains 39.8 g (0.261 mole) of per-p-toluic acid, 152.6 g of solvent ethyl acetate, and 7.58 g (0.055 moles) of p-toluic acid, and 35 g of propylene is fed to the product solution, and subjected to reaction at a temperature of 50° to 52°C for 1 hour.

When the entire amount of the resulting product is distilled, 12.7 g of propylene oxide, 150 g of the solvent, and 42.8 g of p-toluic acid as the bottoms are obtained. Therefore, the selectivity to propylene oxide, based on the per-p-toluic acid, is 83.8% of mole, and the selectivity to p-toluic acid is almost 100%.

Comparative Example 1

When p-tolualdehyde (99% or more) used in Example 1 is used as such without any pretreatment as the oxidation raw material, the following results are obtained. 100 g of untreated p-tolualdehyde and 200 g of dehydrated acetone are charged into an autoclave, and subjected to reaction in the absence of catalyst under the same conditions as in Example 1.

One hour after the start of stirring, the reaction is slowly started, and its reaction rate is low. Thus, it takes 6 to 7 hours until the entire amount of the charged p-tolualdehyde is oxidized.

The resulting reaction product solution is considerably white-turbid, and is in a slurry state. The entire amount of the product solution is 319.5 g. Its per-p-toluic acid content is as low as 18.9% by weight, and its yield based on the charged p-tolualdehyde is 46.5% by mole. More than half of the entire amount of p-tolualdehyde is converted to p-toluic acid, and per-p-toluic acid cannot be efficiently synthesized in high yield, as compared with Example 1.

Comparative Example 2

When the p-tolualdehyde, which has not been subjected to removal of the reaction-inhibiting substances, is used, the reaction rate is low, and the per-p-toluic acid yield is low, as shown in Comparative Example 1, and thus the use of a catalyst is indispensable in an industrial scale production.

Effect of addition of various catalysts is investigated under the feeding conditions of raw material p-tolualdehyde and solvent acetone of Comparative Example 1, and it is found that catalysts of cobalt system are preferable, and $CoCl_2$ is particularly preferable among the cobalt salts.

An optimum amount of the cobalt catalyst as $Co^{2+}$ to be added to the entire amount of the charged solution is 5–6 ppm, and at that time the reaction is completed for 2.5 hours in per-p-toluic acid yield of 76.8% by mole. When the resulting reaction product solution is left standing for 24 hours, the per-p-toluic acid yield is reduced to about 66% by mole due to the decomposition of per-p-toluic acid. However, its reaction rate and yield are low, as compared with the reaction of the pretreated p-tolualdehyde in the absence of catalyst (Examples 1 and 2).

When the cobalt catalyst is added as $Co^{2+}$ in an amount of 18 ppm, the reaction is completed for 1.5 hours, but percentage of production of p-toluic acid as by-product from p-tolualdehyde reaches 32% by mole, whereas the per-p-toluic acid yield of only 65% by mole is obtained. In addition, about 5% by mole of toluene is produced as a by-product. The reaction product solution containing $Co^{2+}$ undergoes gradual change at room temperature, resulting in reduction in the per-p-toluic acid concentration.

Comparative Example 3

To 150.6 g of the product solution containing 30.2% by weight of per-p-toluic acid, obtained in the presence of 5.4 ppm of $Co^{2+}$ in Comparative Example 2 is immediately charged 55 g of propylene. The reaction system is tightly sealed, and the reaction is carried out at a temperature of 50° to 52°C and a stirring rate of 700 rpm for 1 hour.

Said raw material product solution (150.6 g) contains 45.5 g (0.299 moles) of per-p-toluic acid, 11.38 g of p-toluic acid, 1.12 g of toluene, and 92.6 g of solvent acetone, and the amount of the charged propylene corresponds to 4.37 times the moles of the per-p-toluic acid.

After the completion of reaction, unreacted propylene is purged, and the contents are withdrawn from the reaction system. Total amount of the contents is 158.8 g. By distillation of the contents, 11.6 g of propylene oxide, 90.5 g of solvent acetone, and 53.0 g of p-toluic acid as the bottoms are obtained.

Therefore, the selectivity to propylene oxide based on the per-p-toluic acid is 66.9% by mole.

When epoxidation of propylene is carried out under the same conditions as above, using the product solution containing 25.9% by weight of per-p-toluic acid, for example, obtained in the presence of 18 ppm of $Co^{2+}$ in Comparative Example 2, the selectivity to propylene oxide, based on the per-p-toluic acid, is further lowered to 53.5% by mole.

As is apparent from the foregoing, the presence of a catalyst for synthesizing peracids, such as $Co^{2+}$, etc. is not preferable in the epoxidization of propylene by per-p-toluic acid.

EXAMPLE 8

Epoxidation of allyl alcohol is carried out with 200 g of the per-p-toluic acid product solution containing 31.6% by weight of per-p-toluic acid, obtained by autooxidizing p-tolualdehyde with air in the absence of catalyst in acetone as a solvent. That is to say, the per-p-toluic acid product solution contains 63.2 g (0.415 moles) of per-p-toluic acid, 13.2 g (0.097 moles) of p-toluic acid and the solvent acetone. 24.4 g (0.420 mole) of allyl alcohol, which is equimolar to the per-p-toluic acid, is fed to an autoclave containing the per-p-toluic acid product solution, the autoclave being provided with a rotating stirrer and a reflux cooler, and subjected to reaction at a temperature of 50° to 52°C at a stirring speed of 500 rpm for 2 hours.

After the completion of reaction, the autoclave is cooled, and the contents are withdrawn from the autoclave. The total amount of the contents is 219.5 g. The deposited crystals are filtered off, and dried, whereby 54.1 g (0.397 moles) of p-toluic acid is obtained.

Composition analysis of mother liquor reveals that the mother liquor contains 15.4 g (0.113 moles) of p-toluic acid, 28.4 g (0.384 moles) of glycidol, 1.51 g (0.026 moles) of unreacted allyl alcohol, and 120.1 g of acetone, and contains no other by-products almost at all. Therefore, the glycidol yield based on the per-p-toluic acid is 92.8% by mole. On the other hand, the total amount of p-toluic acid is 69.5 g. By deduction of the amount of per-p-toluic acid contained in advance in the raw material product solution from the total amount, 56.3 g (0.415 moles) is obtained, which corresponds to the amount of newly formed p-toluic acid by the epoxidation reaction. Therefore, the p-toluic acid yeild based on the per-p-toluic acid is 99.8% by mole.

Now, description is made of a procedure for recovering p-toluic acid and glycerin from the mother liquor.

Total amount of the mother liquid obtained in this Example is 165.4 g, but 120 g of water is added to 160 g of the mother liquid. Then, the solvent acetone and unreacted allyl alcohol are separated and recovered therefrom by distillation under the atmospheric pressure. Crystals deposited in the bottoms are filtered off, and dried, whereby 13.7 g of p-toluic acid is obtained.

0.5 g of caustic soda is dissolved in the resulting filtrate to make the filtrate solution weakly alkaline, and most of water is removed from the filtrate solution by evaporation under the atmospheric pressure, and successively the filtrate solution is sufficiently dehydrated under a reduced pressure of about 40 mmHg, and then distilled under a reduced pressure of 5 to 6 mmHg, whereby 33.6 g of a fraction of 152° to 160°C is obtained. Said fraction is glycerin having a 98.2% purity.

In terms of the total amount of mother liquor, the p-toluic acid obtained by said treatment amounts to 14.2 g (0.104 moles), and glycerin 34.1 g (0.370 mole) as 100% purity.

Therefore, the product glycerin yield based on the per-p-toluic acid is 89.2% by mole throughout the reaction and separating operations. Glycerin recovery percentage based on glycidol formed by the reaction corresponds to 96.4% by mole.

On the other hand, the total amount of p-toluic acid recovered as crystals throughout the reaction and separating operations is 68.3 g, but by the deduction of the amount of p-toluic acid contained in advance in the charged raw material product solution, the amount of p-toluic acid, which is deemed to be recovered from per-p-toluic acid, is 55.1 g (0.405 moles). Therefore, the ultimate p-toluic acid yield is 97.6% by mole.

EXAMPLE 9

200 g of the same per-p-toluic acid product solution containing 31.6% by weight of per-p-toluic acid as used in Example 8 and 48.2 g (0.830 mole) of allyl alcohol, which corresponds to twice the moles of per-p-toluic acid, are charged into an autoclave, and subjected to reaction at a temperature of 60° to 62°C for 1.5 hours.

After the completion of the reaction, the autoclave is cooled, and the contents are withdrawn from the autoclave. The entire amount of the contents is 243.6 g. Deposited crystals are filtered off from the contents, and dried, whereby 52.0 g (0.382 moles) of p-toluic acid is obtained.

Composition analysis of mother liquor reveals that the mother liquor contains 17.3 g (0.127 moles) of p-toluic acid, 29.7 g (0.401 mole) of glycidol, 24.2 g (0.417 moles) of unreacted allyl alcohol, and 120.4 g of acetone, and contains no other by-products almost at all.

Therefore, the glycidol yield, based on the per-p-toluic acid, is 96.7% by mole. On the other hand, the total amount of p-toluic acid is 69.3 g. By deduction of the amount of p-toluic acid contained in advance in the raw material product solution, the p-toluic acid formed by the epoxidation reaction amounts to 56.1 g (0.412 moles). Therefore, the p-toluic acid yield, based on the per-p-toluic acid, is 99.3% by mole.

Then, recovery of glycerin from the mother liquor and recovery of dissolved p-toluic acid are carried out in the manner as described in Example 8.

As a result, the percent recovery of glycerin from glycidol is 95.5% by mole, and the percent recovery of crystal p-toluic acid from the dissolved p-toluic acid is 92.0% by mole.

Therefore, the glycerin yield, based on the per-p-toluic acid, is 92.3% by mole, and the p-toluic acid yield, based on the per-p-toluic acid, is 96.8% by mole throughout the reaction and separating operations.

EXAMPLE 10

Epoxidation of allyl alcohol is carried out with 200 g of the per-p-toluic acid product solution containing 23% by weight of per-p-toluic acid, obtained by autooxidizing p-tolualdehyde with air in the absence of catalyst in ethyl acetate as a solvent.

That is to say, the per-p-toluic acid product solution contains 46 g (0.302 moles) of per-p-toluic acid, 1.86 g (0.014 moles) of p-toluic acid, and the solvent ethyl acetate. 35.2 g (0.606 moles) of allyl alcohol is fed to the per-p-toluic acid product solution in an autoclave, and subjected to reaction at a temperature of 60° to 62°C for 2 hours.

After the completion of reaction, the contents are withdrawn from the autoclave, and the total amount of the contents is 230.4 g. Deposited crystals are filtered off from the contents, and dried, whereby 33.5 g (0.246 moles) of p-toluic acid is obtained. Composition analysis of mother liquid reveals that the mother liquor contains 8.92 g (0.066 moles) of p-toluic acid, 20.8 g (0.281 mole) of glycidol, 17.9 g (0.308 moles) of unreacted allyl alcohol and 149.4 g of ethyl acetate, and contains no by-products especially from the standpoint of quantitative problem.

Therefore, the glycidol yield, based on the per-p-toluic acid, is 93% by mole, and the p-toluic acid yield, based on the per-p-toluic acid, is 96.2% by mole.

Glycerin and p-toluic acid can be obtained with similar percent recovery by the same operations of separating the respective components as in Example 8.

EXAMPLE 11

To 200 g of the per-p-toluic acid product solution containing 27.4% by weight of per-p-toluic acid, obtained by autooxidizing p-tolualdehyde with air in acetone as a solvent, is fed allyl alcohol in an equimolar amount to the per-p-toluic acid, and epoxidation of allyl alcohol is carried out in the presence of various compounds of transition metal as a catalyst.

Reaction conditions and results are shown in the following Table.

Table

| Test run No. | Catalyst | Amount added (ppm) | Temp. (°C) | Time (hr) | Per-p-toluic acid conversion (%) | Selectivity to p-toluic acid (%) | Selectivity to glycidol (%) |
|---|---|---|---|---|---|---|---|
| 1 | None | none | 56 | 2.0 | 99.6 | 99.8 | 93.1 |
| 2 | V naphthenate (3% V) | 5.0 | 50 | 1.8 | 99.8 | 99.5 | 90.4 |
| 3 | $V_2O_5$ | 5.0 | 50 | 1.5 | 99.2 | 99.6 | 89.0 |
| 4 | Mo naphthenate (4% Mo) | 7.0 | 50 | 1.5 | 99.9 | 99.2 | 87.5 |
| 5 | $CoCl_2 \cdot 4H_2O$ | 5.0 | 50 | 1.5 | ~100 | 99.5 | 88.2 |
| 6 | $FeCl_2$ | 10.0 | 55 | 1.8 | 99.5 | 99.1 | 72.4 |
| 7 | $WO_2$ | 10.0 | 50 | 1.5 | ~100 | 99.2 | 77.7 |

Note: Percentage in Table is by mole.

Epoxidation of allyl alcohol similarly proceeds even in the presence of various other catalysts such as Ta naphthenate, Nb naphthenate, $TiCl_4$, $NiCl_2$, etc.

EXAMPLE 12

Esterification of methanol is carried out with 100 g of per-p-toluic acid crystals obtained by distilling off acetone from the per-p-toluic acid product solution, obtained by autooxidizing p-tolualdehyde with air in the absence of catalyst in acetone as a solvent.

The per-p-toluic acid crystals contain 72.7 g (0.478 moles) of per-p-toluic acid and 27.3 g (0.201 mole) of p-toluic acid. Said per-p-toluic acid crystals, 217.3 g (6.79 moles) of methanol, which corresponds to 10 times the total moles of the charged per-p-toluic acid and p-toluic acid, and 3.14 g of 98 wt.% concentrated sulfuric acid are charged into a threeneck flask of 500-ml capacity provided with a rotating stirrer and a reflux cooler, and subjected to reaction at a temperature of 64° to 65°C for 2 hours.

After the completion of reaction and cooling, composition analysis of the resulting reaction product solution is carried out, which reveals that the reaction product solution contains 11.6 g (0.341 mole) of hydrogen peroxide, 82.1 g (0.547 moles) methyl p-toluate, 16.7 g (0.123 moles) of p-toluic acid, and 3.7 g (0.206 moles) of water, in addition to methanol and catalyst sulfuric acid, but contains no by-products almost at all.

Therefore, the hydrogen peroxide yield, based on the charged per-p-toluic acid, is 71.3% by mole. On the other hand, the methyl p-toluate yield, based on the total moles of the charged per-p-toluic acid and p-toluic acid contained in advance in the raw material crystals, is 80.6% by mole. The percent residue as p-toluic acid is 18.1% by mole.

EXAMPLE 13

Description is made of a procedure for separating and recovering hydrogen peroxide and methyl p-toluate individually from the reaction product solution obtained in Example 12.

The amount of the reaction product solution is 318.2 g, and to avoid a risk of explosion at the recovery of methanol, 8 g of water is added to the reaction product solution, and 199.0 g (6.22 moles) of methanol is recovered from the solution by distillation. As a result, the remaining solution is separated into an aqueous layer containing hydrogen peroxide and an organic layer of methyl p-toluate containing p-toluic acid.

The organic layer obtained from the lower layer contains methyl p-toluate, p-toluic acid and 0.29 g (0.016 moles) of hydrogen peroxide formed by the reaction. Water is added to the organic layer to recover hydrogen peroxide by extraction, and then the organic layer freed from hydrogen peroxide is subjected to simple distillation, whereby almost all the amounts of methyl p-toluate as a distillate and p-toluic acid as bottoms are recovered, respectively.

On the other hand, the aqueous layer contains hydrogen peroxide, water and sulfuric acid, and contains no substantial amount of methyl p-toluate and p-toluic acid. From the aqueous layer is obtained 22.8 g of 47.8 wt.% of hydrogen peroxide by distillation. Therefore, the percent recovery of hydrogen peroxide from the aqueous layer is 94.4% in all the hydrogen peroxides formed by the reaction.

EXAMPLE 14

Esterification of methanol is carried out with the per-p-toluic acid product solution containing 30.0% by weight of per-p-toluic acid, obtained by autooxidizing p-tolualdehyde with air in the absence of catalyst in acetone as a solvent.

That is to say, said per-p-toluic acid product solution containing 60.0 g (0.394 moles) of per-p-toluic acid, 22.5 g (0.165 moles) of p-toluic acid, and acetone, 89.6 g (0.280 mole) of methanol, which corresponds to four times the total moles of the charged per-p-toluic acid and p-toluic acid, and 1.44 g of 98 wt.% by weight of concentrated sulfuric acid are charged into a reactor. At first, acetone is recovered from the reaction mixture at the boiling point (56.3°C) of acetone and then the reaction mixture is subjected to reaction at a temperature of 64° to 65°C for 2.5 hours.

After the completion of reaction and cooling, the resulting reaction product solution is analyzed. The reaction product solution contains 9.20 g (0.271 mole) of hydrogen peroxide, 68.2 g (0.454 moles) of methyl p-toluate, 11.8 g (0.087 moles) of p-toluic acid and 3.3 g (0.183 moles) of water in addition to methanol and sulfuric acid, and contains no by-products almost at all.

Therefore, the hydrogen perxoide yield, based on the charged per-p-toluic acid, is 68.8% by mole. On the other hand, the methyl p-toluate yield, based on the total moles of the charged per-p-toluic acid and the p-toluic acid contained in advance in the raw material product solution, is 81.3% by mole. Percent residue as p-toluic acid is 15.6% by mole.

Then, 6 g of water is added to 82.1 g of the reaction product solution, and recovery of hydrogen peroxide and methyl p-toluate is carried out in the same manner as in Example 13. As a result, 18.1 g of 48.1 wt.% hydrogen peroxide is obtained from an aqueous layer. Therefore, 94.5% of the hydrogen peroxide formed by the reaction is recovered from the aqueous layer. On the other hand, almost all the amounts of methyl p-toluate and p-toluic acid formed by the reaction are recovered from the organic layer, individually.

EXAMPLE 15

100 g of per-p-toluic acid crystals having the same composition as used in Example 12, 217.3 g (6.79 moles) of methanol, which corresponds to ten times the total moles of the charged per-p-toluic acid and p-toluic acid, and 50 g of strongly acidic cation exchange resin as a catalyst (Amberlite IR-120, trademark of a product made by Rohm and Haas Co., U.S.A.) are charged into a reactor and subjected to reaction at a temperature of 64° to 65°C for 2.5 hours.

After the completion of reaction and cooling, the contents are withdrawn from the reactor, and the catalyst is removed from the contents by filtration. The amount of the reaction product solution freed from the catalyst is 315.8 g. Analysis of the reaction product solution reveals that it contains 11.4 g (0.335 moles) of hydrogen peroxide, 82.7 g (0.551 mole) of methyl p-toluate, 16.3 g (0.120 mole) of p-toluic acid, 3.9 g (0.217 moles) of water and methanol, and contains no by-product almost at all.

Therefore, the hydrogen peroxide yield, based on the charged per-p-toluic acid, is 70.1% by mole. On the other hand, the methyl p-toluate yield, based on the total moles of the charged per-p-toluic acid and the p-toluic acid contained in advance in the raw material crystals, is 81.1% by mole. The percent residue as p-toluic acid is 17.7% by mole.

Then, 7.5 g of water is added to the reaction product solution, and methanol is recovered from the solution in the same manner as in Example 13, whereby 22.5 g of 49.3 wt.% hydrogen peroxide is obtained from an aqueous layer. Therefore, 97.3% of hydrogen peroxide formed by the reaction is recovered.

On the other hand, methyl p-toluate and p-toluic acid formed by the reaction are recovered from an organic layer with similar percent recovery to that of Example 13, individually.

What is claimed is:

1. A process for producing per-p-toluic acid, which comprises autooxidizing p-tolualdehyde, free of reaction inhibiting substances, in the form of a solution having a concentration of 10 to 50% by weight of p-tolualdehyde in a solvent of acetone or ethylacetate with a gas containing molecular oxygen, the autooxidation being conducted at a temperature of 10° to 50°C and under a pressure of 1 to 60 kg/cm$^2$ gage.

2. The process according to claim 1, wherein the p-tolualdehyde contains less than 300 ppm of aromatic hydrocarbons less than 200 ppm of non aromatic hydrocarbons, less than 300 ppm of high boiling point substances and less than 5 ppm of acidic substances.

3. The process according to claim 1, wherein the gas containing molecular oxygen is air.

* * * * *